United States Patent [19]  [11] 4,287,890
Fogarty  [45] Sep. 8, 1981

[54] ENDARTERECTOMY METHOD

[76] Inventor: Thomas J. Fogarty, 770 Welch Rd., Palo Alto, Calif. 94304

[21] Appl. No.: 114,980

[22] Filed: Jan. 24, 1980

[51] Int. Cl.³ .............................................. A61B 17/00
[52] U.S. Cl. ................................ 128/303 R; 128/319; 128/321
[58] Field of Search ............... 128/321, 322, 325, 346, 128/303 R, 305, 319, 57, 60

[56] References Cited
U.S. PATENT DOCUMENTS 2,944,552  7/1960  Cannon ................................ 128/304
3,648,701  3/1972  Botts ................................... 128/321

Primary Examiner—Robert W. Michell
Assistant Examiner—Michael H. Thaler
Attorney, Agent, or Firm—Naylor, Neal & Uilkema

[57] ABSTRACT

Arteriosclerotic material is stripped free from an artery by clamping the artery between a pair of opposed roller elements and moving the roller elements along the length of plaque segment to be removed. A tapered edge is first formed at the leading end of the plaque segment to provide a working edge for the roller instrument.

4 Claims, 7 Drawing Figures

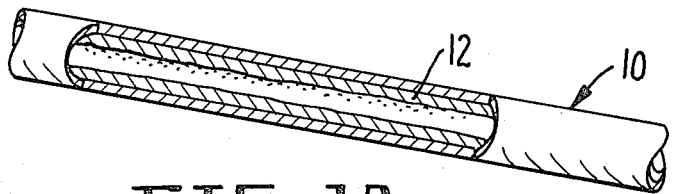
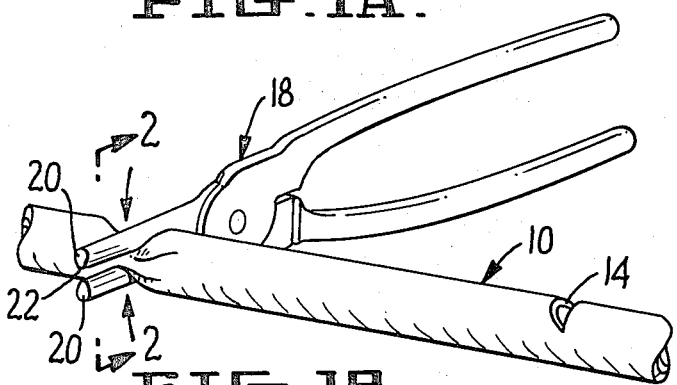
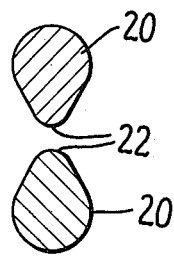
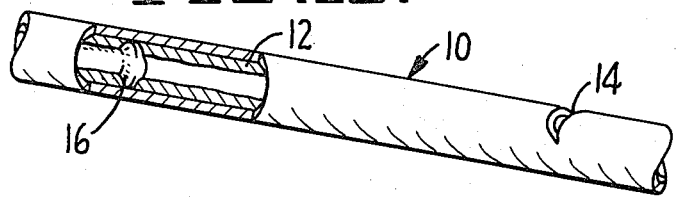
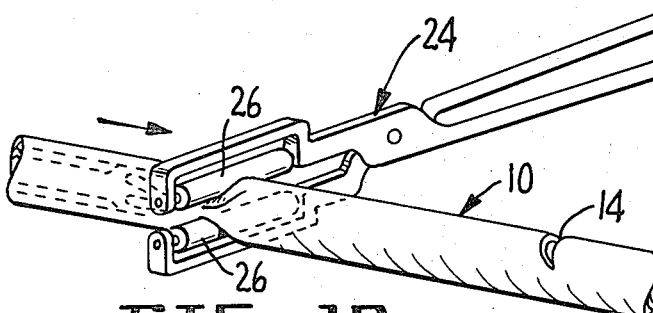
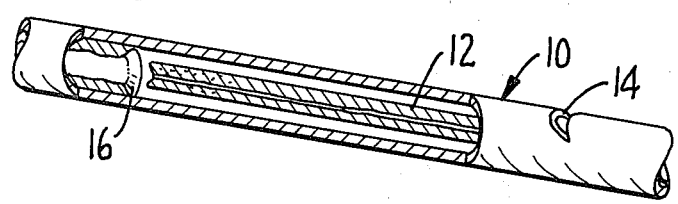
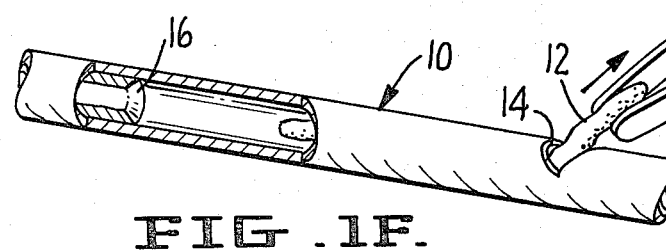

ENDARTERECTOMY METHOD

BACKGROUND OF THE INVENTION

The invention relates to a method and means for removing an extended length of arteriosclerotic material from the lumen of an occluded artery.

I am not aware of any prior art which is material to the subject invention. The subject invention is characterized by stripping the arteriosclerotic material from an artery by squeezing the artery between a pair of rollers and moving the rollers along the artery. The prior art endarterectomy methods known to me comprise the use of annular knives or cutting loops which are moved along the inside of an artery to excise the arteriosclerotic occlusion therefrom.

I am aware that roller-pair instruments have been disclosed, as in U.S. Pat. Nos. 3,648,701 and 4,164,223, as a means for stripping the contents of flexible tubing prior to the use of such tubing, for example, for intravenous feeding.

SUMMARY OF THE INVENTION

Among the general objects of the invention are the following: to decrease operating time and avoid extensive suturing in the performance of endarterectomies and to provide for complete removal of arteriosclerotic material over a given segment of artery.

A specific object of the invention is to provide a new and improved method whereby arteriosclerotic material may be stripped free from the wall of an artery by stripping means applied to the artery exteriorly thereof.

DESCRIPTION OF THE PREFERRED EMBODIMENT

Figure 1A:
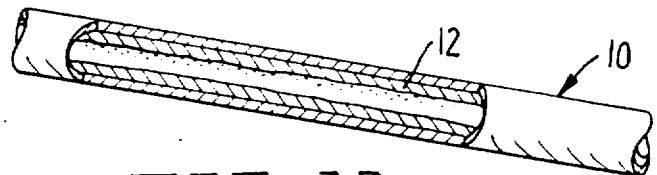
FIG. 1A is a broken away view in perspective of an occluded artery.
Figure 2:
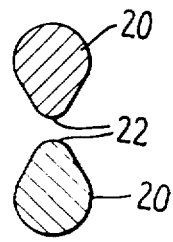
FIG. 2 is an enlarged detail view of the crimping instrument of FIG. 1B taken along lines 2—2 thereof.

In the drawing, the artery 10 contains a section of arteriosclerotic material 12. The artery is provided with an incision 14 adjacent one end of the material 12.

Figure 1B:
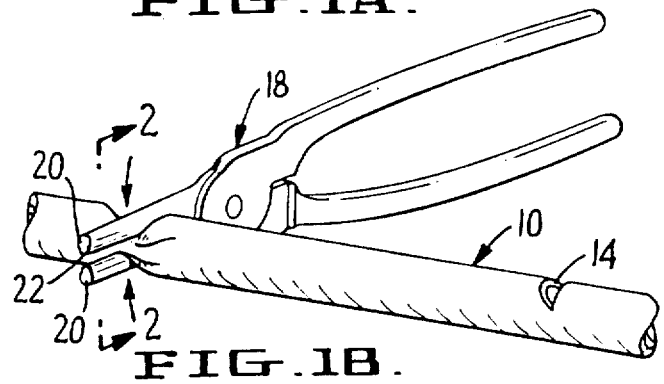
FIG. 1B shows the same artery during the crimping step of the subject method.
Figure 1C:
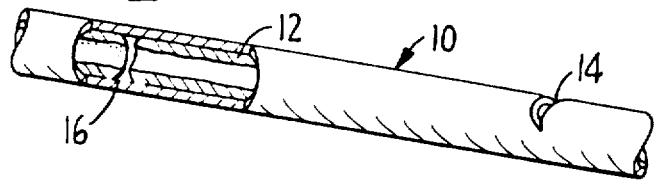
FIG. 1C is a broken away view of the same artery showing the shape of the crimp formed in the arteriosclerotic material by the crimping step of FIG. 1B.

The first step in method is to form an annular groove 16 in the material 12. This is accomplished by applying the crimping tool 18 in clamping relation to the artery 10, as in FIG. 1B, and working the tool through 360° along the same crimping line. The jaws 20 of tool 18 are provided with relatively thin, rounded crimping edges 22. The groove 16 in the core 12 of atheromatous plaque serves to divide the plaque into separate sections having tapered edges. Tapering of the ends of the plaque sections enables them to be removed during the subsequent roller-stripping step while reducing the possibility of a thrombosis resulting as a consequence of the practice of the subject endarterectomy method.

Figure 1D:
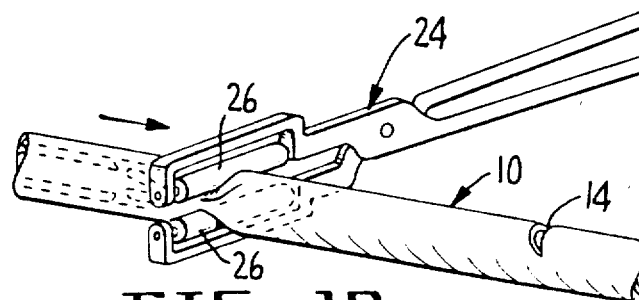
FIG. 1D is a view similar to FIG. 1B but showing the roller stripping instrument in position for the occlusion-stripping step of the method.
Figure 1E:
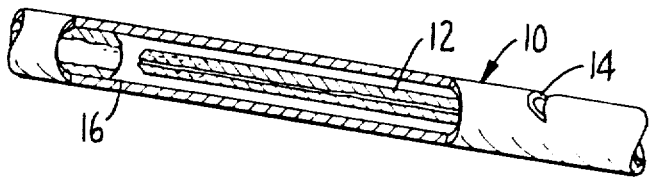
FIG. 1E is a view similar to FIG. 1C but showing the arteriosclerotic material stripped free from the wall of the artery.
Figure 1F:
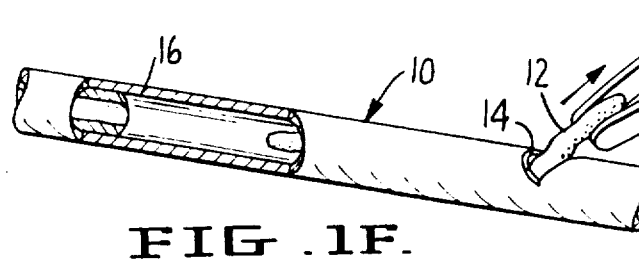
FIG. 1F is a view similar to FIG. 1E illustrating the manner in which the stripped material is removed from the artery.

The next step in the method is the application of the endarterectomy roller instrument 24 to the artery at the plaque separation line constituted by the apex of groove 16, said instrument comprising a pair of rollers 26. The instrument 24 is then moved while in the closed position shown in FIG. 1D past the plaque end located adjacent incision 14. This results in the plaque being stripped free from the wall of the artery, as shown in FIG. 1E. The plaque is then removed from the artery through the incision by means of forceps 28.

The pressure exerted by the roller instrument 24 on the artery as the instrument is moved therealong in closed position serves to free the arteriosclerotic core from the artery. The complemental shapes of the rollers 26 and the tapered end edge of the core material 12 serves to effect stripping removal of the core material while minimizing breaking up or fragmenting of the material 12 with possibly consequent thrombosis.

What is claimed is:

1. A method for freeing arteriosclerotic occlusions from arteries comprising crimping the artery to form a tapered end edge on an occlusion segment, clamping the artery between a pair of roll-like elements disposed in pressing relation with said end edge, and moving said elements to the distal end of said occlusion segment.

2. The method of claim 1, further comprising removing said segment from the artery by forming an incision in the artery adjacent the digital end of said segment, and pulling said segment through said incision.

3. A method for freeing an arteriosclerotic occlusion from an artery comprising pre-conditioning said artery and occlusion by crimping them to form substantially separate occlusion segments having tapered end edges substantially complemental to the working surface portions of hereinafter mentioned roll-like elements, forming incisions in said artery adjacent the ends of said occlusion, clamping the artery between a pair of roll-like elements at the location of said tapered end edges, moving said elements in clamped condition from said location, first in one direction past an end of said occlusion and then in the other direction past the other end of said occlusion, and removing the occlusion material from the artery through said incisions.

4. A method for freeing arteriosclerotic occlusions from arteries comprising laterally compressing the artery in a zone of compression to form a tapered end edge on an occlusion segment, and stripping said occlusion segment from said artery by causing said zone of compression to progressively traverse said segment from said tapered end edge to the distal end of said segment.

* * * * *

UNITED STATES PATENT AND TRADEMARK OFFICE
CERTIFICATE OF CORRECTION

PATENT NO. : 4,287,890

DATED : Sept. 8, 1981

INVENTOR(S) : Thomas J. Fogarty

It is certified that error appears in the above—identified patent and that said Letters Patent is hereby corrected as shown below:

The Drawing shown in the original patent should appear as in the attached sheet.

Signed and Sealed this

Twenty-fifth Day of March 1986

[SEAL]

Attest:

DONALD J. QUIGG

Attesting Officer

Commissioner of Patents and Trademarks